United States Patent [19]

Suzuki et al.

[11] Patent Number: 5,413,776
[45] Date of Patent: May 9, 1995

[54] PHARMACEUTICAL PREPARATION FOR PERCUTANEOUS ABSORPTION

[75] Inventors: Taro Suzuki; Mutsumi Fukuda; Kunio Yoneto, all of Osaka, Japan

[73] Assignee: Sekisui Chemical Co., Ltd., Osaka, Japan

[21] Appl. No.: 64,361

[22] Filed: Dec. 22, 1992

Related U.S. Application Data

[63] Continuation of Ser. No. 750,803, Aug. 19, 1991, abandoned.

[51] Int. Cl.$^6$ .............................. A61F 13/02
[52] U.S. Cl. ................... 424/448; 424/449; 514/946; 514/947
[58] Field of Search ............... 424/448, 449; 514/946, 514/947

[56] References Cited

U.S. PATENT DOCUMENTS

| | | | |
|---|---|---|---|
| 4,455,146 | 6/1984 | Noda et al. | 424/449 |
| 4,751,087 | 6/1988 | Wick | 424/446 |
| 4,781,926 | 11/1988 | Hyon et al. | 424/486 |
| 4,789,667 | 12/1988 | Makino et al. | 514/161 |
| 4,906,475 | 3/1990 | Kim | 424/449 |
| 5,032,402 | 7/1991 | Digenis | 424/448 |

FOREIGN PATENT DOCUMENTS

| | | |
|---|---|---|
| 0201828 | 11/1986 | European Pat. Off. . |
| 58-79918 | 5/1983 | Japan . |
| 59-199628 | 11/1984 | Japan . |
| 1199628 | 11/1984 | Japan . |
| 60-66759 | 4/1985 | Japan . |
| 60-123417 | 7/1985 | Japan . |
| 60-185713 | 9/1985 | Japan . |
| 61-260028 | 11/1986 | Japan . |

*Primary Examiner*—D. Gabrielle Phelan
*Attorney, Agent, or Firm*—Armstrong, Westerman, Hattori, McLeland & Naughton

[57] ABSTRACT

The present invention provides a pharmaceutical preparation for percutaneous absorption comprising a drug-impermeable substrate having provided thereon an adhesive layer comprising a drug and a drug dissolution aid, characterized in that said adhesive is composed of a copolymer essentially consisting of 5 to 35 wt % of N-vinyl-2-pyrrolidone and 65 to 95 wt % of an acrylic acid ester, 3 to 30 wt % of a homopolymer of N-vinyl-2-pyrrolidone is contained in said adhesive layer as the drug dissolution aid, and said drug is a hydrophilic drug having a saturation solubility of 6 to 50 wt % to N-vinyl-2-pyrrolidone. Where the hydrophilic drug is Piroxicam, it is preferred to use a polyoxyethylene alkyl ether and/or a fatty acid alkylolamide as an absorption enhancer in combination.

9 Claims, No Drawings

PHARMACEUTICAL PREPARATION FOR PERCUTANEOUS ABSORPTION

This application is a continuation of application Ser. No. 750,803 filed Aug. 27, 1991, now abandoned.

BACKGROUND OF THE INVENTION

1. Field of the Invention

The present invention relates to a pharmaceutical preparation for percutaneous absorption comprising a substrate having provided thereon an adhesive layer containing a relatively hydrophilic drug and more particularly, to a preparation for percutaneous absorption which is used as a plaster having a high percutaneous absorption of a drug over long periods of time and having a difficultly decreasing adhesiveness over long periods of time.

2. Statement of the Prior Art

Pharmaceutical preparations for percutaneous absorption. have many advantages as compared to oral administration in that they can avoid liver metabolism, can maintain blood concentration of a drug in a definite range over long periods of time, can be used in a simple fashion, etc. Among preparations for percutaneous absorption, a plaster is an extremely desirable preparation since a dose can be set in a definite range, a plaster itself has a high adhesive force, one has a low feeling of foreign matter with a plaster upon use and there is no chance of getting clothes dirt.

However, the skin plays a role of protecting the living body to prevent invasion of a foreign matter into the body and hence, in many cases, it is difficult to percutaneously administer a drug in a sufficient dose into the body. Therefore, it is necessary to take measures such as increasing an area to be applied, increasing an amount of a drug to be permeated per unit area, and the like. However, an excessively increased area to be applied results in inconvenience upon use or a high feeling of foreign matter so that practicability is damaged. It is thus automatically limited to increase the area. On the other hand, in order to increase an amount of a drug to be permeated per unit area, there are many proposals that a drug concentration in a base or an adhesive layer is increased, an absorption enhancer is added, etc. An increased concentration of a drug in a base is an effective means since drug permeability can be maintained in a high level over long periods of time. However, the solubility of a hydrophilic drug is low in a general adhesive so that an increase in drug concentration in a base results in crystallization on the surface or in the inside of a base. Formation of drug crystals results in a serious decrease in adhesiveness and in many hydrophilic drugs, releasability from a base is also markedly reduced. That is, many hydrophilic drugs encounter serious problems that a drug concentration in a base is increased only with difficulty, and there is no adhesive capable of maintaining these drugs in a high concentration.

In order to solve the foregoing problems, it is proposed in Japanese Patent Application Laid-Open No. 61-260028 to use poly-N-vinyl-lactam or a copolymer of N-vinyl-lactam as one component of the therapeutically active compound-releasing system using as a base an adhesive having physical properties of a rubber. It is taught that these components in a base of rubber type adhesive prevent from crystallization a therapeutically active compound in the therapeutically active compound-releasing system or at least greatly retarding the crystallization.

Where the rubber type adhesive is used as a base, however, there is a poor compatibility between the rubber type adhesive and poly-N-vinyl-lactam or a copolymer of N-vinyl-lactam so that stability of the resulting matrix is deteriorated with passage of time. Unless the matrix is stable with passage of time, the applicability and releasability of a plaster are also unstable, and these situations are serious problems as a drug. Furthermore, in the case of a hydrophilic drug, its solubility in a rubber type adhesive is extremely low so that the rubber type adhesive is not suited for increase a drug concentration, either.

Turning to Japanese Patent Application Laid-Open No. 60-185713, there is proposed a method which comprises applying a solution of adhesive containing a drug on one surface of a substrate and crystallizing crystals of the drug during a subsequent drying step thereby to disperse the crystals in a base in a finely divided particulate state. However, many drugs have an extremely low dissolution rate of a drug in a base from a crystalline state. Therefore, this method cannot be generalized for all drugs.

Topical plasters using, e.g., Piroxicam, are described in Japanese Patent Application Laid-Open Nos. 63-159318 and 3-109327. However, drug concentrations in solid preparations found in these examples are as low as 1% or less and 3% or less, respectively. It is thus difficult to maintain a necessary amount of the drug in a base over long periods of time.

It is particularly advantageous to add an absorption enhancer, since the enhancer improves a drug permeability. For example, Japanese Patent Application Laid-Open No. 61-172833 indicates that by using phospholipid as an absorption enhancer in combination with a non-steroidal antiinflammatory agent in percutaneous administration, percutaneous absorption is increased. However, such an effect is not recognized with all drugs; a percutaneous absorption enhancing action of phospholipid is insufficient for, e.g., Piroxicam and hence, any sufficient therapeutic effect cannot be expected.

SUMMARY OF THE INVENTION

A first object of the present invention is to provide a pharmaceutical preparation for percutaneous absorption which is stable with passage of time and enables to incorporate a hydrophilic drug in a base in a high concentration, without forming crystals of the drug on the surface and/or inside of the base.

A second object of the present invention is to provide a preparation for percutaneous absorption which comprises Piroxicam as the drug and has an excellent drug-releasing property to the skin.

Where an adhesive is composed of a copolymer obtained by copolymerizing N-vinyl-2-pyrrolidone (hereafter abbreviated as VP) with a (meth)acrylic acid ester, an increased ratio of VP to be copolymerized results in improvement in the solubility of a hydrophilic drug but its pressure-sensitive adhesiveness decreases. According to investigations by the present inventors, however, it has been surprisingly found that a composition comprising a copolymer of a definite amount of VP with a (meth)acrylic acid ester and a homopolymer of N-vinyl-2-pyrrolidone (hereafter abbreviated as PVP) can improve the solubility of a hydrophilic drug without reducing its pressure-sensitive adhesiveness. The present invention has been made based on such a finding.

The preparation for percutaneous absorption of the present invention comprises a drug-impermeable substrate having provided thereon an adhesive layer, i.e., a base, comprising a drug and a drug dissolution auxiliary agent, characterized in that:

said adhesive comprises a copolymer mainly obtained from 5 to 35 wt % of N-vinyl-2-pyrrolidone and 65 to 95 wt % of a (meth)acrylic acid ester, 3 to 30 wt % of a homopolymer of N-vinyl-2-pyrrolidone is contained in the adhesive layer as the drug dissolution auxiliary agent, and, the drug is a hydrophilic drug having a saturation solubility to N-vinyl-2-pyrrolidone of 6 to 50 wt %.

In the preparation for percutaneous absorption according to the present invention, the adhesive may be composed of a copolymer obtained from 5 to 35 wt % of N-vinyl-2-pyrrolidone, 65 to 95 wt % of a (meth)acrylic acid ester and 0 to 10 wt % of a copolymerizable third monomer and/or 0 to 0.5 wt % of a polyfunctional monomer.

A representative example of the hydrophilic drug having the aforesaid saturation solubility is Piroxicam. Of course, other drugs may be used.

The preparation for percutaneous absorption according to the present invention preferably contains an absorption enhance in the adhesive layer. Where the drug is Piroxicam, polyoxyethylene alkyl ethers or fatty acid alkylolamides are preferably used as the absorption enhancer.

According to the present invention, the following effects or advantages are provided. That is, PVP which is a polymer of VP is contained as the drug dissolution auxiliary agent in the adhesive layer which comprises a copolymer consisting essentially of VP and a (meth)acrylic acid ester and has a pressure-sensitive adhesiveness at normal temperature. There is thus provided the preparation for percutaneous absorption which is stable with passage of time and contains a hydrophilic drug in a high concentration in such a state that crystals of the drug are not formed on the surface and/or in the inside of the base. The hydrophilic drug used in the present invention shows a high solubility even in the adhesive layer containing a VP-(meth)acrylic acid ester copolymer alone, as compared to a rubber type adhesive, and also shows a high solubility in VP. Therefore, the drug concentration in the adhesive layer can be more increased due to the effect of PVP. As the result, there can be provided a pharmaceutical preparation for percutaneous absorption having a greatly improved drug releasability to the skin, without reducing its adhesiveness.

DETAILED DESCRIPTION OF THE PREFERRED EMBODIMENTS

In the present invention, the adhesive is composed of a copolymer obtained mainly from 5 to 35 wt % of VP and 65 to 95 wt % of a (meth)acrylic acid ester and has a pressure-sensitive adhesiveness at normal temperature.

According to the present invention, it is important that all of the VP component are not copolymerized with the (meth)acrylic acid ester but a part of the VP is added to the copolymer as PVP. In general, when the VP component is all subjected to copolymerization, the saturation solubility of a hydrophilic drug increases to a certain extent but a serious decrease in adhesiveness is unavoidable. In the present invention, a part of the VP component is mixed with the copolymer in the form of PVP so that the solubility of a hydrophilic drug greatly increases but the adhesiveness is hardly reduced.

Preferred examples of the (meth)acrylic acid ester which can be used in the present invention include an acrylic acid ester having 3 to 10 carbon atoms in the alkyl moiety and a methacrylic acid ester having 8 to 12 carbon atoms in the alkyl moiety; specific examples are propyl acrylate, butyl acrylate, isobutyl acrylate, hexyl acrylate, heptyl acrylate, 2-ethylbutyl acrylate, octyl acrylate, 2-ethylhexyl acrylate, decyl acrylate, nonyl acrylate, octyl methacrylate, decyl methacrylate, lauryl methacrylate, etc. Particularly preferred are 2-ethylhexyl acrylate, butyl acrylate, hexyl acrylate, heptyl acrylate, octyl acrylate and decyl methacrylate.

When a ratio of VP to be copolymerized is too small, compatibility of the copolymer with PVP is insufficient; conversely where the ratio is too large, a pressure-sensitive adhesiveness is damaged. For this reason, VP is incorporated in a copolymerization ratio of 5 to 35 wt %, preferably 10 to 30 wt %, based on the total monomer.

In the present invention, a copolymerizable monomer may be used as a third component in a range of 10% or less, for the purposes of controlling polymerization property or physical property of the adhesive. Examples of the copolymerizable monomer include vinyl acetate, styrene, acrylonitrile, acrylamide, dimethylaminoacrylate, butyl maleate, acrylic acid, and methacpylic acid.

In the present invention, a polyfunctional monomer may be copolymerized in a range of 0.5 wt % or less, for the purposes of improving internal cohesive force of the adhesive layer. When the amount exceeds 0.5 wt %, the adhesive tends to cause gelation and sometimes adversely affect compatibility with PVP used as the drug dissolution auxiliary agent. As the polyfunctional monomer, there are di(meth)acryaltes, tri(meth)acrylates, tetra(meth)acrylates, etc. Specific examples include di(meth)acrylates obtained by reacting polymethylene glycols such as hexamethylene glycol, etc. with (meth)acrylic acid; di(meth)acrylates obtained by reacting polyalkylene glycols such as polyethylene glycol, polypropylene glycol, etc. with (meth)acrylic acid; tri(meth)acrylates such as trimethylolpropane tri(meth)acrylate, glycerine tri(meth)acrylate, etc.; tetra(meth)acrylates such as pentaerythritol tetra(meth)acrylate, etc. These polyfunctional monomers may be used in combination of two or more.

The copolymer of the present invention is obtained generally by solution polymerization but the mode of polymerization is not limited thereto. As a solvent for polymerization, ethyl acetate is preferably used. As a polymerization initiator, there may be appropriately used azobis type initiators, e.g., 2,2'-azobisisobutyronitrile, 1,1'-azobis(cyclohexane-1-carbonitrile), etc.; peroxide type initiators, e.g., benzoyl peroxide, lauroyl peroxide, etc.

A molecular weight of the copolymer is not particularly limited but in general, the copolymer having 100,000 to 2,000,000 (weight-average molecular weight by gel permeation chromatography, when calculated as polystyrene) may be used advantageously.

PVP which is used as the drug dissolution auxiliary agent generally has an average moleculer weight of 10,000 to 2,000,000. PVP is incorporated in an amount of 3 to 30 wt %, preferably 5 to 20 wt %, in the adhesive layer composed of the copolymer described above. When the content of PVP is too small, the effect of improving the solubility of a drug is poor; conversely when the content is too large, adhesiveness decreases and compatibility with the copolymer decreases.

The drug which can be used in the present invention is a hydrophilic drug having the saturation solubility of 6 to 50 wt % to vinyl pyrrolidone monomer. The reason why the upper limit of the saturation solubility of a drug to vinyl pyrrolidone monomer is 50 wt % is that: when the saturation solubility exceeds 50 wt %, the amount of a drug in the base is excessively large to reduce adhesiveness, assuming that the drug is incorporated in its saturation solubility. The reason why the lower limit for the saturation solubility of a drug is 6 wt % is because the advantage of the present invention for maintaining a drug in a high concentration is not sufficiently exhibited with the amount of less than 6 wt %. Among such hydrophilic drugs, a drug having a low solubility in the (meth)acrylic acid ester monomer (for example, 6 wt % or less in the saturation solubility to the (meth)acrylic acid ester monomer) is particularly preferred because the solubility in the adhesive composed of the copolymer alone described above is not enough.

Examples of the drug which can be used in the present invention include Piroxicam, Indometacin, Triamcinolone, Acetaminophen, Fenbufen, Sodium Tolmetin, Haloperidol, Propranolol Hydrochloride, Estradiol, Clonidine Hydrochloride, Tetracycline, Chloramphenicol, Fradiomycin Sulfate, Nifedipine, Clotrimazole, Benzalkonium Chloride, Nystatin, Nikolandyl, Ephedrine Hydrochloride, Hydrocortison, Diphenhydramine HCl Fluocinolone Acetonide, etc. However, the drug which may be used is not limited thereto. The content of a drug is appropriately determined depending upon use; the upper limit of the drug content is set so as not to cause crystallization of the drug on the surface and/or in the inside of the base during storage even over a long period of time. In general, the drug is contained in an amount of 5 to 30 wt % in the adhesive layer.

In the present invention an absorption enhancer may be incorporated appropriately in the adhesive layer, if necessary. Examples of the absorption enhancer include alkyl esters such as isopropyl myristate, diethyl sebacate, etc.; glycols such as propylene glycol, 1,3-butylene glycol, etc.; alcohols such as ethanol, stearyl alcohol, etc.; organic acids such as oleic acid, stearic acid, etc. and salts thereof; urea, and the like.

Where the drug is Piroxicam, polyoxyethylene alkyl ethers and fatty acid alkylolamides are preferred as the absorption enhancer, As the polyoxyethylene alkyl ethers, there may be used compounds represented by general formula:

R—O—(CH$_2$CH$_2$)nH wherein R is an alkyl group and n is 2 to 50, usually 2 to 20. Preferred alkyl groups shown by R have 1 to 20 carbon atoms, and are, e.g., methyl, ethyl, propyl, butyl, pentylr hexyl, heptyl, octyl, nonyl, decyl, dodecyl, lauryl, myristyl, palmityl, stearyl, isopropyl, cetyl, or t-butyl group, etc.

Examples of the fatty acid alkylolamides are acid amides obtained from fatty acids such as caproic acid, caprylic acid, capric acid, lauric acid, stearic acid, arachidoic acid, hexadecenic acid, oleic acid, myristic acid, palmitic acid, lanileic acid, etc. with alkylolamines such as monoethanolamine, diethanolamine, isopropanolamine, etc. A representative example is lauric acid diethanolamide. These absorption enhancers may be used singly or in combination of two or more.

The absorption enhancer may be contained in the adhesive layer, usually in an amount of 30 wt % or less, preferably 15 wt % or less.

When the absorption enhancer is polyoxyethylene alkyl ethers or fatty acid alkylolamides described above, it may be contained usually in an amount of 0.5 to 10 wt %, preferably 1 to 6 wt % in the adhesive layer.

The preparation for percutaneous absorption of the present invention may appropriately contain in the adhesive layer, if necessary, an tackif let such as rosin, terpene resin, etc.; a softener such as wax, oils and fats, etc.; a filler such as titanium oxide, calcium carbonate, etc.

The substrate in the present invention may be any material so long as it is drug-impermeable and flexible. A sheet, a film, a metal foil or a laminate thereof, woven cloth, non-woven cloth, etc. may be used. Examples of the material are ethylene-vinyl acetate copolymer, polyurethane, polyesters such as polyethylene terephthalate, etc.; polyamides such as nylon 6, etc.; polyethylene, plasticized polyvinyl chloride, polyvinylidene chloride, vinyl acetate-vinyl chloride copolymer, cellulose acetate, ethyl cellulose, aluminum, etc. A laminate film of polyethylene terephthalate and ethylene-vinyl acetate copolymer or a polyurethane film may be advantageously employed due to adaptability to the movement of the skin. A thickness of the substrate is 500 μm or less, preferably 5 to 100 μm.

To obtain the preparation for percutaneous absorption of the present invention, for example, the following procedures may be taken. Firstly, the copolymer described above is dissolved in an appropriate solvent, and PVP is..dissolved in an appropriate solvent. The two solutions are combined and a hydrophilic drug and, if necessary, an absorption enhancer, are added to the solution mixture to dissolve them. Then, an adhesive layer is formed on the substrate in a conventional manner, using the resulting adhesive solution containing the drug.. The preparation for percutaneous absorption of plaster type is thus prepared.

EXAMPLES

Hereafter the present invention is described with reference to non-limiting examples. Example 1

In a separable flask were charged 360.0 parts by weight of 2-ethylhexyl acrylate (EHA), 40.0 parts by weight of N-vinyl-2-pyrrolidone (VP) and 0.08 part by weight of hexamethylene glycol dimethacrylate. Then 400.0 parts by weight of ethyl acetate was added to the mixture. The solution was heated at 60° C. in a nitrogen atmosphere and a solution of 2.5 parts by weight of lauroyl peroxide as a polymerization initiator in 200 parts by weight of cyclohexane-ethyl acetate mixture was added to the solution by about 1/6 volume every 2 other hours, whereby polymerization was carried out for 12 hours. After withdrawing from the separable flask, the reaction product was dried at 105° C. for 4 hours to give about 400 parts by weight of solid copolymer. Tetrahydrofuran (THF) was added to 100 parts by weight of this solid copolymer in a polymer concentration of about 25 wt % to dissolve the copolymer. A solution of 3.5 parts by weight of polyvinylpyrroliaone (PVP) (weight-average molecular weight: about 1,100,000, "Kolltdon 90 ®" made by BASF) in 10.0 parts by weight of ethanol was added to the resulting solution. As a hydrophilic drug, 11.5 parts by weight of Nifedipine (which solubility was 28wt % in VP and 0.5wt % in EHA) was added to the mixture. Furthermore, THF was added thereto to have 25 wt % in total of the copolymer, PVP and Nifedipine. A coating solution was thus prepared.

The coating solution was coated onto a silicone-treated polyethylene terephthalate strippable liner to form a thickness of 80 μm after,drying, By. drying at 60° C. for 30 minutes, an adhesive layer was formed. A substrate composed of a laminate film of polyethylene terephthalate (PET) and ethylene-vinyl acetate copolymer was laminated with the adhesive layer on the PET surface. A plaster was thus prepared.

Comparative Example 1

A plaster was prepared in a manner similar to Example 1 except that PVP was not added to the copolymer.

Comparative Example 2

360.0 parts by weight of EHA, 53.3 parts by weight of VP and 0.08 part by weight of hexamethylene glycol dimethacrylate were copolymerized with each other, whereby the whole amount of VP was provided for copolymerization to give a solid copolymer. No PVF was added to the copolymer. A plaster was prepared otherwise in a manner similar to Example 1.

Example 2

A solid copolymer was obtained in a manner similar to Example 1 except that 320.0 parts by weight of hexyl acrylate (HA) and 80.0 parts by weight of VP were used. To 100 parts by weight of this solid copolymer was added THF in a polymer concentration of about 25 wt % thereby to dissolve the copolymer. A solution of 17.7, parts by weight of PVP (weight-average molecular weight about 45,000, "Kollidon 30 ®" made by BASF) in 53.0 parts by weight of ethanol was added to the resulting solution. After 20.8 parts by weight of Estradioi (which solubility was 27 wt % in VP and 0.5 wt % in HA) was added as a hydrophilic drug, THF was added to the mixture to have 25 wt % in total of the copolymer, PVP and Estradiol. A coating solution was thus prepared. A plaster was prepared in a manner similar to Example 1, using this coating solution.

Example 3

A solid copolymer was obtained in a manner similar to Example 1 except that 280.0 parts by weight of butyl acrylate (BA) and 120.0 parts by weight of VP were used. To 100 parts by weight of this solid copolymer was added THF in a polymer concentration of about 25 wt % thereby to dissolve the copolymer. A solution of 25.0 parts by weight of PVP (weight-average molecular weight : about 29,000, "Kollidon 25 ®" made by BASF)in 100.0 parts by weight of ethanol was added to the resulting solution. After 22.1 parts by weight of Indometacin (which solubility was 38 wt % in VF and 0.7 wt % in BA) was added as a hydrophilic drug, THF was added to the mixture to have 25 wt % in total of the copolymer PVP and Indometacin. A coating solution was thus prepared. A plaster was prepared in a manner similar to Example 1, using this coating solution.

Example 4

A solid copolymer was obtained in a manner. similar to Example 1 except that 302.0 parts by weight of Ella and 98.0 parts by weight of VP were used. To 100 parts by weight of this solid copolymer was added THF in a polymer concentration of about 25 wt % thereby to dissolve the copolymer. A solution of 11.1 parts by weight of PVP (weight-average molecular weight : about 1,100,000, "Kollidon 90 ®" made by BASF). in 33.3 parts by weight of ethanol was added to the resulting solution. After 20.9 parts by weight of Piroxicam (which solubility was 6.5 wt % in VP and 0.3 in EHA) as a hydrophilic drug and 7.1 parts by weight of isopropyl myristate were added to the mixture, THF was added to the mixture to have 25 wt % in total of the copolymer, PVP, Piroxicam and isopropyl myristate. A coating solution was thus prepared. A plaster was prepared in a manner similar to Example 1, using this coating solution.

Comparative Examples 3 to 5

Plasters were prepared in a manner similar to Examples 2 to 4, respectively, except that no PVP was added to the copolymer.

Comparative Example 6

A plaster was prepared in a manner similar to Example 4 except that the mixture of 50.0 parts by weight of natural rubber ("TPC ®" made in Sri Lanka, purchased from Ito Trading Co.) and 50.0 parts by weight of polyterpene type resin ("YS Resin ®" made by Yasuhara Yushi Co.) was used instead of the solid copolymer in Example 4.

Example 5

A solid copolymer was obtained by performing the reaction in a manner similar to Example 1 except that 302.0 parts by weight of EHA, 98.0 parts by weight of VP and 0.08 part by weight of hexamethylene glycol dimethacrylate were used. To 100 parts by weight of this solid copolymer was added THF in a polymer concentration of about. 25 wt % thereby to dissolve the copolymer. A solution of 11.1 parts by weight of PVP (weight-average molecular weight: about 1,100,000, "Kollidon 90 ®" made by BASF) in 33.3 parts by weight of ethanol was added to the resulting solution. After 20.9 parts by weight Of Piroxicam, 4.7 parts by weight of polyoxyethylene (2) lauryl ether and 2.4 parts by weight of isopropyl myristate were added to the mixture, respectively, THF was further added to the mixture to have 25 wt % in total of the copolymer, PVP, Piroxicam, polyoxyethylene (2) lauryl ether and isopropyl myristate. A coating solution was thus prepared. A plaster was prepared in a manner similar to Example 1, using this coating solution.

Example 6

A solid copolymer was obtained by performing the reaction in a manner similar to Example 1 except that 320.0 parts by weight of hexylacrylate and 80.0 parts by weight of VP were used. To 100 parts by weight of this solid copolymer was added THF in a polymer concentration of about 25 wt % thereby to dissolve the copolymer. A solution of 8.7 parts by weight of PVP (weight-average molecular weight: about 45,000, "Kollidon 30 ®" made by BASF) in 26.1 parts by weight of ethanol was added to the resulting solution. After 12.5 parts by weight of Piroxicam and 3.4 parts by weight of lauric acid diethanolamide were added to the mixture, THF was further added to the mixture to have 25 wt % in total of the copolymer, PVP, Piroxicam and lauric acid diethanolamide. A coating solution was thus prepared.

A plaster was prepared in a manner similar to Example 1, using this coating solution.

Example 7

A solid copolymer was obtained by performing the reaction in a manner similar to Example 1 except that 802.0 parts by weight of butyl acrylate (BA) and 8.0 parts by weight of VP were used. To 100 parts by weight of this solid copolymer was added THF in a polymer concentration of about 25 wt % thereby to dissolve the copolymer. A solution of 11.1 parts by weight of PVP (weight-average molecular weight: about 29,000, "Kollidon 25 ®" made by BASF) in 33.3 parts by weight of ethanol was added to tile resulting solution. After 17.3 parts by weight of Piroxicam and 4.6 parts by weight of polyoxyethylene (7) oleyl ether were added to the mixture, THF was further added to the mixture to have 25 wt % in total of the copolymer, PVP Piroxicam and polyoxyethylene (7) oleyl ether. A coating solution was thus prepared. A plaster was prepared in a manner similar to Example 1, using this coating solution.

Comparative Examples 7 to 9

Plasters were prepared, respectively, in a manner similar to Examples 5 to 7 except that no PVP was added to the copolymer.

Evaluation

With respect to each plaster obtained in the Examples and the Comparative Examples, a state of crystallizing the drug, adhesiveness and skin permeability were evaluated by the following methods.

The state of crystallizing the drug was observed with a biological microscope (magnification: ×400) after transferring the adhesive layer of a test: piece onto a slide glass.

Test of the adhesiveness was carried out as follows, by a modification of the ball tack test defined in JIS Z0237-1980. A paper sheet is attached to the both edges of a test piece of 10 cm wide and 10 cm long so as to remain the central part of the adhesive surface on the test piece by 5 cm to the longitudinal direction. The test piece is fastened with a pin on the 30° slope of a tester, turning the adhesive surface up. A ball defined in JIS B1501 is rolled from 10 cm upward of the upper side of the exposed adhesive surface. By changing a size of the ball, rolling is repeated to find the biggest ball which stops on the adhesive surface. Adhesiveness is expressed by the number of this ball.

Test of the skin permeability was performed as follows. Immediately after nude mouse (age of 8 weeks, male) was sacrificed, the skin at the back was peeled apart to remove the subcutaneous fat and the muscle layer. Thus, a skin piece of approximately 5 cm ×6 cm was obtained. The skin piece was set on a Franz diffusion cell, putting its stratum copneum layer side up. A test piece punched into an area of 3.14 $cm^2$ was applied to the upper surface of the skin piece after the strippable liner was removed. The diffusion cell was then kept at 37° C. and a receptor solution was agitated. An amount of the drug permeated into the receptor solution 24 hours after onset of the test was determined by high performance liquid chromatography. The number of the test pieces was 3 each per preparation.

The results are shown in Table 1.

TABLE 1

| | State of Crystallization of Drug | Ball Number in Test of Adhesiveness | Amount Permeated through Skin (mg/100 $cm^2$, 24 hrs) |
|---|---|---|---|
| Example 1 | none | 11 | not measured |
| Example 2 | none | 12 | 1.5 |
| Example 3 | none | 15 | 3.9 |
| Example 4 | none | 16 | 3.2 |
| Example 5 | none | 20 | 8.7 |
| Example 6 | none | 16 | 8.0 |
| Example 7 | none | 15 | 8.5 |
| Comparative Example 1 | crystallized | 5 | not measured |
| Comparative Example 2 | crystallized | 6 | not measured |
| Comparative Example 3 | crystallized | less than 3 | 0.5 |
| Comparative Example 4 | crystallized | less than 3 | 1.2 |
| Comparative Example 5 | crystallized | less than 3 | 0.9 |
| Comparative Example 6 | crystallized* | less than 3 | 0.3 |
| Comparative Example 7 | crystallized | less than 3 | 1.6 |
| Comparative Example 8 | crystallized | less than 3 | 1.6 |
| Comparative Example 9 | crystallized | less than 3 | 1.8 |

*indicates that compatibility between rubber adhesive and PVP was poor and the adhesive layer was not uniform even by visual observation.

Stability of the preparation was evaluated by putting a test piece in an aluminum laminate film-made bag, sealing the bag, storing the test piece at 60° C. for 2 weeks and then observing the state of crystallization of the drug, performing the test of adhesiveness and the test of skin permeability as described above.

The results of the stability test are shown in Table 2.

TABLE 2

Stability (after storage for 2 weeks at 60° C.)

| | State of Crystallization of Drug | Ball Number in Test of Adhesiveness | Amount Permeated through Skin (mg/100 $cm^2$, 24 hrs) |
|---|---|---|---|
| Example 2 | none | 11 | 1.6 |
| Example 3 | none | 15 | 3.9 |
| Example 4 | none | 17 | 3.2 |
| Example 5 | none | 20 | 8.9 |
| Example 6 | none | 16 | 8.2 |
| Example 7 | none | 16 | 8.4 |
| Comparative Example 3 | crystallized | less than 3 | 0.4 |
| Comparative Example 4 | crystallized | less than 3 | 1.4 |
| Comparative Example 5 | crystallized | less than 3 | 0.9 |
| Comparative Example 6 | crystallized* | less than 3 | 0.1 |
| Comparative Example 7 | crystallized | less than 3 | 1.3 |
| Comparative Example 8 | crystallized | less than 3 | 1.2 |
| Comparative Example 9 | crystallized | less than 3 | 1.4 |

*indicates that compatibility between rubber adhesive and PVP was poor and the adhesive layer was not uniform even by visual observation.

While the invention has been described in detail and with reference to specific embodiments thereof, it is apparent to one skilled in the art that various changes and modifications can be made therein without departing from the spirit and the scope of the present invention.

What is claimed is:

1. A pharmaceutical preparation for percutaneous absorption of a drug comprising a drug-impermeable substrate having provided thereon an adhesive layer composed of
   a copolymer consisting essentially of 5 to 35 wt % of N-vinyl-2-pyrrolidone and 65 to 95 wt % of an acrylic acid ester, and containing 3 to 30 wt % of a homopolymer of N-vinyl-2-pyrrolidone as a dissolution agent for the drug, and
   5 to 30 wt % of a hydrophilic drug having a saturation solubility of 6 to 50 wt % in N-vinyl-2-pyrrolidone.

2. A preparation according to claim 1, wherein said adhesive is composed of a copolymer obtained from 5 to 35 wt % of N-vinyl-2-pyrrolidone, 65 to 95 wt % of a (meth)acrylic acid ester, 0 to 10 wt % of a copolymerizable third monomer and/or 0 to 0.5 wt % of a polyfunctional monomer.

3. A preparation according to claim 1 or 2, wherein said hydrophilic drug is Piroxicam.

4. A Preparation according to claim 1, wherein said adhesive layer contains 0 to 15 wt % of an absorption enhancer.

5. A preparation according to claim 4, wherein said absorption enhancer is a polyoxyethylene alkyl ether and/or a fatty acid alkylolamide.

6. A preparation according to claim 5, wherein each content of polyoxyethylene alkyl ether and/or fatty acid alkylolamide is 1 to 6 wt % of adhesive layer.

7. A preparation according to claim 3, wherein said adhesive layer contains 0 to 15 wt % of an absorption enhancer.

8. A preparation according to claim 7, wherein said absorption enhancer is a polyoxyethylene alkyl ether and/or a fatty acid alkylolamide.

9. A preparation according to claim 8, wherein each content of polyoxyethylene alkyl ether and/or fatty acid alkylolamide is 1 to 6 wt % of adhesive layer.

* * * * *